United States Patent
Dewan

(10) Patent No.: US 6,529,773 B1
(45) Date of Patent: Mar. 4, 2003

(54) COMMUNICATION AND CONTROL BY MEANS OF BRAINWAVE AND OTHER PROCESSES CAUSING VOLTAGE CHANGES THAT CAN BE MEASURED FROM THE BODY

(75) Inventor: Edmond M. Dewan, Lexington, MA (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 09/918,800

(22) Filed: Aug. 1, 2001

(51) Int. Cl.[7] .................................................. A61B 5/04

(52) U.S. Cl. .................................................... 600/544

(58) Field of Search ................................. 600/544–545

(56) References Cited

U.S. PATENT DOCUMENTS

| 4,928,704 A | | 5/1990 | Hardt | |
|---|---|---|---|---|
| 5,465,729 A | | 11/1995 | Bittman | |
| 5,474,082 A | * | 12/1995 | Junker | 600/545 |
| 5,638,826 A | * | 6/1997 | Wolpaw et al. | 600/544 |
| 5,740,812 A | | 4/1998 | Cowan | |
| 6,097,981 A | * | 8/2000 | Freer | 600/545 |
| 6,246,322 B1 | * | 6/2001 | Torch | 341/121 |

* cited by examiner

Primary Examiner—Robert L. Nasser
Assistant Examiner—Patricia Mallari
(74) Attorney, Agent, or Firm—William G. Auton

(57) ABSTRACT

People can be taught to control voluntarily their own alpha rhythms. This can be used to send messages in Morse code and printed out by printer when an electroencephalogram pattern is processed by an appropriate computer program. Such procedures can also be used as control signals to activate servomechanisms any other device or appliance.

6 Claims, 7 Drawing Sheets

X CYBERNETICS
EI

FIG. 3

COMMUNICATION AND CONTROL BY MEANS OF BRAINWAVE AND OTHER PROCESSES CAUSING VOLTAGE CHANGES THAT CAN BE MEASURED FROM THE BODY

STATEMENT OF GOVERNMENT INTEREST

The invention described herein may be manufactured and used by or for the Government for governmental purposes without the payment of any royalty thereon.

BACKGROUND OF THE INVENTION

The invention relates generally to the fields of electroencephalographic (EEG) monitoring and biofeedback, and more specifically to biofeedback devices and techniques for operating binary digit communication systems and controlling servomechanisms.

Telepathy and telekinesis are the subjects of science fiction and magic tricks such as that of U.S. Pat. No. 4,443,010, entitled, Psychic connection game by Larwood. A more serious development was described by Martin Caidin in his book "The God Machine" who said, "Scientists at the Cambridge Research Laboratories had worked for years in brainwave communications experiments. Dr. Edmond M. Dewan trained skilled volunteers to alter the pattern of the alpha-wave rhythm of the brain, the low-frequency wave related to visual perception. Being able to turn on or off, at will, the alpha rhythm meant an interruption of an electrical source from the brain. By amplifying brainwave signals it was possible for these "alpha adepts" to conduct a crude binary digit system of communications."

Biofeedback systems suitable for use are described in the following U.S. Patents the disclosures of which are incorporated herein by reference.

U.S. Pat. No. 6,097,981, Aug. 1, 2000, Electroencephalograph based biofeedback system and method, Freer, Peter A., U.S. Pat. No. 5,740,812, Apr. 21, 1998, Apparatus for and method of providing brainwave biofeedback, Cowan, Jonathan D., U.S. Pat. No. 5,465,729, Nov. 14, 1995, Method and apparatus for biofeedback, Bittman, U.S. Pat. No. 4,928,704, May 29, 1990, EEG biofeedback method and system for training voluntary control of human EEG activity, Hardt, James V.

SUMMARY OF THE INVENTION

People can be taught to control voluntarily their own alpha rhythms. This can be used to send messages in Morse code when an electroencephalogram pattern is analyzed by a computer program. Such procedures can also be used as control signals to activate devices.

The present invention includes a brainwave controlled optical communication system that uses volitionally altered oculomotor states to modulate an EEG control signal and activate a light transmitter. This system uses scalp electrodes for sensing EEG control signals from a user that has been instructed to selectively alter his or her alpha-wave rhythms of his or her brain by an eye positioning technique and produce thereby a predetermined EEG control signal pattern corresponding to a Morse code message.

The Freer EEG transmitter is used as a means for transmitting an optical communication signal which is activated by the EEG control signals from the sensing means. The Freer receiver is used as a receiver which receives and displays the optical communication signal of the transmitting means.

DESCRIPTION OF THE DRAWINGS

FIG. 3 shows a word transmitted by brainwaves.

DESCRIPTION OF THE PREFERRED EMBODIMENT

The present invention includes a dynamically operated biofeedback communication and control system that operates a binary digit communication system and controls servomechanisms using the brainwaves of a system operator. As mentioned above, scientists in the past, at what was then known as the Air Force at the Cambridge Research Laboratories, have worked in brainwave communications experiments. Dr. Edmond M. Dewan trained skilled volunteers to alter the pattern of the alpha-wave rhythm of the brain, the low-frequency wave related to visual perception. Being able to turn on or off, at will, the alpha rhythm meant an interruption or "blocking" of an electrical oscillation from the brain. By amplifying brainwave signals it was possible for these subjects to conduct a binary digit system of communications under experimental conditions. Dewan's preliminary results were documented in Nature, Vol. 214, p. 975 is an article entitled "Occipital Alpha Rhythm Eye Position and Lens Accommodation" (1967) which is incorporated by reference. His principles are put into application here.

Figure 1:
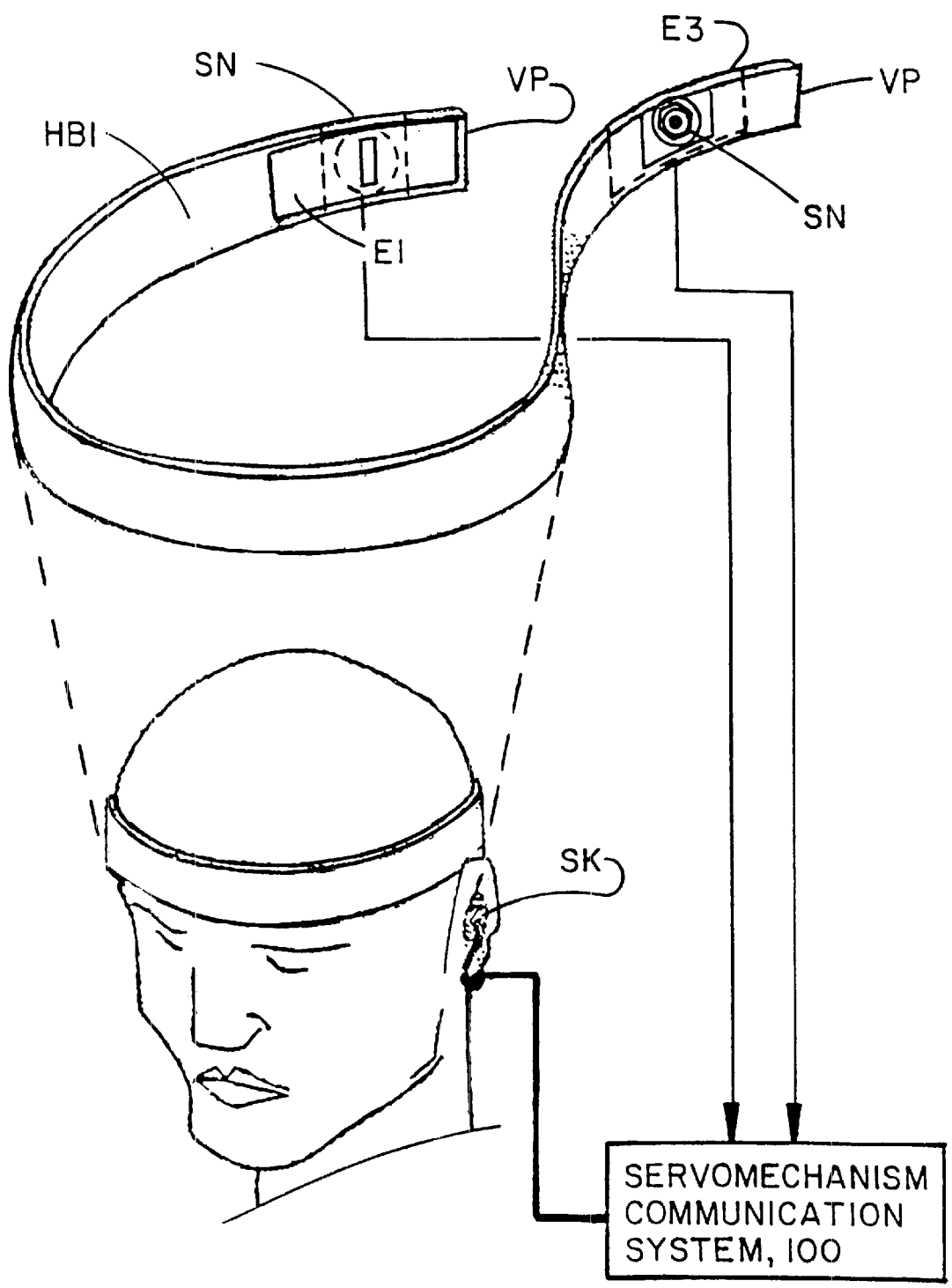
FIG. 1 is a biofeedback system applied to control a communication system or servomechanism.

The reader's attention is now directed towards FIG. 1 which depicts a biofeedback sensor system which is worn on the head via a strap HB1 and uses two sensors SN to detect the emission of alpha waves and drive a communication system or servomechanism 100. FIG. 1 is a perspective view of a two-electrode implementation. Conductive standard EEG electrodes E1 and E3 are sewn inside headband HB1. Electrodes E1 and E3 are applied in the usual way (with electrode paste) and contact the user's scalp across the occipital lobes, and pick up signals from this area of the brain. Electrodes E1 and E3 are connected via snaps SN to electronics servomechanism communication system 100. In-the-ear audio biofeedback transducer SK is hard-wired to servomechanism 100.

Servomechanism 100 connects to sense electrodes E1 and E3 (which contact the scalp across the back of the head) over the occipital lobe via snaps SN. Headband HB1 is free to slide back and forth through loop-shaped electrodes E1 and E3, allowing the headband to shift some without moving the electrodes. Headband HB1 is fastened via hook and loop type fastener patches VP.

FIG. 1 is an illustration of a biofeedback sensing system which is applying EEG signals to trigger a communication system or a servomechanism 100 and for the present application they must be placed on the back of the head. What is unique about the present invention is the application of eye position principles in order to achieve the desired EEG output and control results, as described below.

The "blocking" or attenuation of occipital alpha rhythms has been associated with "attention" since the discovery of electroencephalography. Many conditions favor the appearance of these rhythms such as eye closure, pattern-less visual fields if eyes are open and, of primary importance, a lack of ocular fixation. On the other hand, such things as pattern vision, ocular fixation, intense concentration on mental tasks or on non-visual stimuli and the perception of surprising, alerting, or affective stimuli favor the "abolition" of alpha activity. This much was shown in 1934 and has been confirmed many times since then. On the other hand, interpretation of these facts has been quite varied.

One original interpretation was that alpha "blocking" results from attention in general. When Adrian and Matthews subsequently found that alpha activity was generated in the occipital lobe rather than from the entire brain, and that it was "blocked" far more effectively by visual than by non-visual activity, they advanced the idea that non-visual "blocking" was caused by a spread of desynchronizing activity from other areas to the occipital lobe. They also explained the effects of eye opening and closure on the alpha rhythms by the presence or absence of visual attention. A similar explanation was used for alpha blocking by the deliberate accommodation and convergence of the eyes (or "looking") in complete darkness or with eyes closed. This view seems to be generally accepted today, although there have been additional variations. For example, Cobb has proposed that pattern vision may cause the blocking response by the series of momentary stimuli resulting from repeated fixation and accommodation. These would act only momentarily, as in the case of unexpected stimuli, but would have a continuous effect because of rapid repetition. It is significant that he found that this happened when something had to be kept in focus, as noted the subjective sensation of accommodation and convergence when they attempted to block activity in the absence of visual stimulation, that is, in darkness or with eyes closed.

More recent experiments have raised additional questions regarding the role of attention. For example, researchers noted that the blocking response was not in one to one correspondence with either attention or visualization and that, as was also noted earlier, considerable mental activity and attention are possible without this response. In addition some workers have reported that the blocking response does not correlate significantly with measures of efficacy of perception or attentiveness. Of especial interest is the observation that in some cases during intense auditory alertness the alpha rhythms can appear, but in this situation they were accompanied by "loss of ocular fixation and accommodation". He therefore proposed that the blocking response represents an "increase of specific visual alertness which may be but one component of general arousal". Still more recently, it was noted that eye position can play an important part in alpha rhythm activity, the extreme upward position tending greatly to enhance it. As will be shown here, one can entertain the hypothesis that this effect may be caused by a tendency of the eyes to defocus and relax convergence when in the maximum upward position. This would be consistent with the observation that the presence of alpha activity is accompanied by absence of fixation and accommodation as well as the remark that alpha activity is never present during fixation.

The main purpose of this patent is to show that it is possible voluntarily to control one's alpha activity by the manipulation of oculomotor configuration and accommodation with accuracy sufficient to send Morse code to a computer and to have the latter type out the corresponding letters automatically on a teleprinter, and to reexamine the "attention hypothesis" in the light of this demonstration.

The procedure was as follows. A "Grass model 7 Polygraph" was used to record occipital electroencephalogram activity with one pair of transcortical bipolar paste electrodes over the left and right occipital areas. This signal was passed through a 10 c/s band pass filter sufficiently broad to pass the alpha activity of all the subjects studied. This filtered signal was fed to a Schmitt trigger which generated a pulse each time the signal voltage exceeded a threshold so adjusted that during the presence of significant alpha activity there was a pulse for each wave crest. This output was fed to a 'LINC' computer which was programmed to ignore "drop ins" (spurious pulse trains) or "drop outs" (short interruptions of pulse trains) of the duration indicated in Table I. It was also programmed to decide on the basis of duration whether or not a dot or dash was being sent, to display this information acoustically and/or visually, to decide on the basis of and to translate the Morse character into its alphabetical equivalent. It then displayed the letter on a cathode ray tube in the subject's field of vision, deleted the complete letter (assumed incorrect), whenever the subject sent a sufficiently prolonged dash, or caused the teleprinter to type out the letter on completion of the succeeding one.

The subject was placed in a screened, acoustically isolated room and provided with the following types of feedback: (1) he could hear the Schmitt trigger output through a loudspeaker; (2) he was informed of the registration of dots and dashes through an intercom or, in the case of subject C.H., he was given this information automatically by audio-signals triggered by the computer; (3) he could check his results by viewing the cathode ray tube through a window. (As expected, it was found that this could be done without spurious generation of alpha activity.)

The subject was instructed to control his alpha activity by the following technique. For maximum voltage he was to turn his eyes to the extreme upward position consistent with comfort and avoid fixation or convergence and accommodation. For minimum or "blocked" activity he was either to open his eyes and fixate them on a nearby object (C.H. and S.M.) or else to keep his eyes closed and fixate them on an imaginary point located almost immediately in front of his lids. (E.D.).

TABLE 1

| Subject | Sec/correct letter | No. of errors | No. of letters | Dot-dash dividing time in 1/9 sec | Inter-character interval in 1/9 sec | Drop-out drop-in time in 1/9 sec |
|---|---|---|---|---|---|---|
| C. H. | 49 | 16 | 26 | 26 | 56 | 4 |
|  | 35 | 13 | 26 | 26 | 56 | 4 |
| S. M. | 48 | 9 | 15 | 34 | 50 | 6 |
|  | 34.6 | 10 | 26 | 20 | 60 | 6 |
| E. D. | 33.6 | 4 | 26 | 34 | 50 | 6 |

Figure 3:
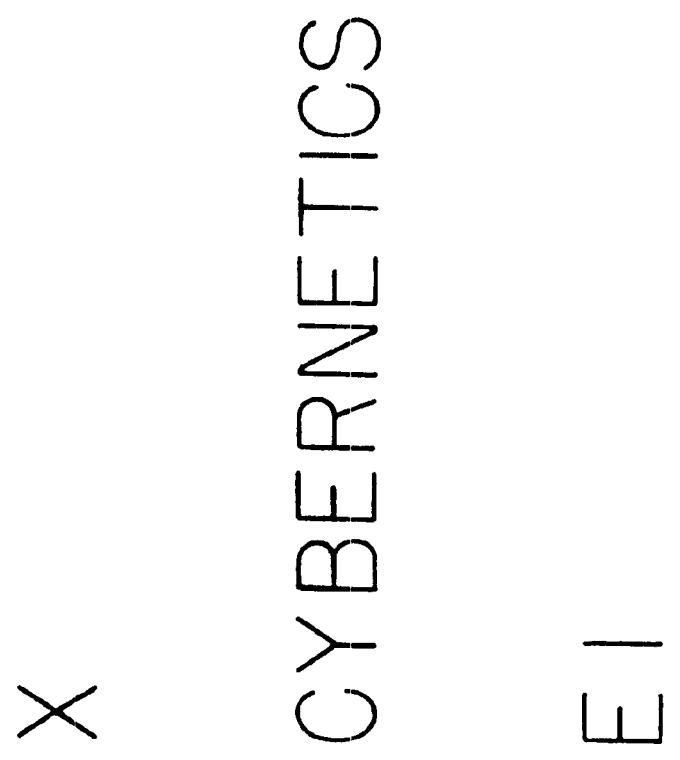
Figure 4:
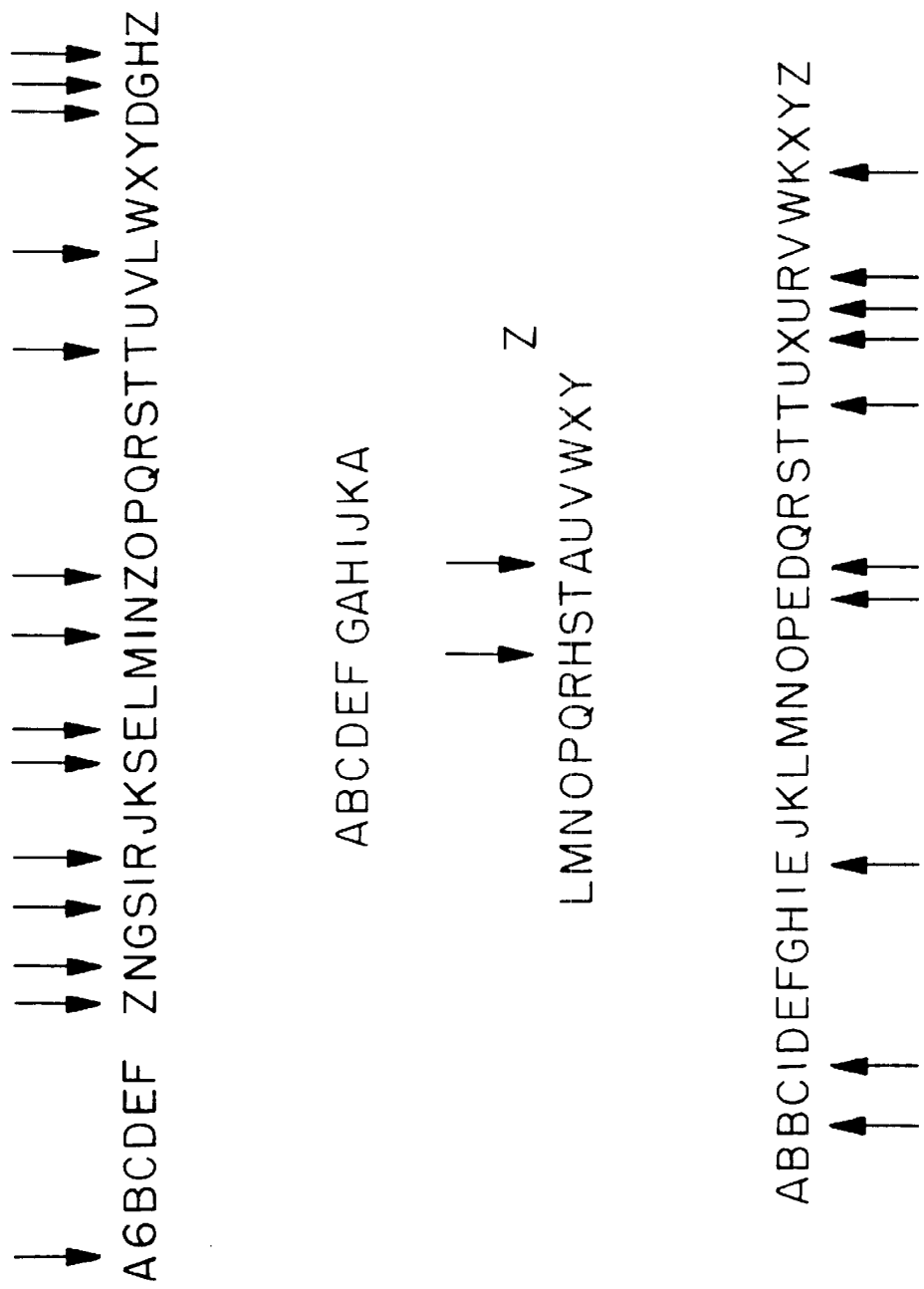
FIG. 4 shows a print out of these subjects sending the alphabet by means of brainwaves.

The observations and results were as follows: FIGS. 2a and 2b show electroencephalograph recordings of subject E.D. while sending Morse code with eyes closed. FIG. 2c shows the effect of the 10 c/s filter on the signal in FIG. 2b. FIG. 3 shows a word typed out using the deleted feature of the program to remove errors before print out. FIG. 4 shows the print out for three subjects attempting to send the alphabet without corrections. Table 1 gives the corresponding times used, number of errors, and computer parameter settings. As can be seen, 35 sec is about the minimum average time needed for each correct letter. Of interest is the "drop in-drop out time" (on the order of 0.5 sec) which gives a measure of the duration during which alpha activity might spontaneously disappear during eye elevation or spontaneously appear during eye fixation. Because this parameter was not very carefully adjusted to optimize performance and because it was used for both the "drop in" and "drop out" durations, it can be considered as being only a rather crude measure of a stochastic component superposed on the voluntary control.

It was further observed that preliminary practice was necessary, external influences could be distracting, and that the subjects reported occasional difficulties in remembering the number of dots and dashes just sent and this accounted for some of the errors in performance. Acoustic feedback had to be low in volume and the subject had to become habituated to it in order to avoid uncontrolled blocking response; several hours of this task proved to be very fatiguing. Finally, it was found that merely turning the closed eyes to an extreme elevation did not results in alpha activity if one focused and converged one's eyes in that position. Fixation or accommodation and convergence had to be avoided to prevent the blocking response. As indicated, this result was incorporated in the technique used by the subjects in this experiment. It would be difficult to interpret these results if one were to assume that the alpha rhythm is blocked or "unblocked" exclusively by some sort of attention mechanism; because, during the experiment, the subject was in a state of constant attention. He was forced to listen attentively to the acoustic feedback and to keep track of what he was "sending". Subjectively, he was not consciously manipulating his attention but instead, his accommodation, convergence and eye elevation. Although cyclomydril, a drug causing pupilary dilation and preventing accommodation, seemed to have no effect on the ability of one subject (E.D.) to send Morse code, it would be interesting to know the effects of other drugs such as curare. If curare prevented the sending of Morse code (and yet allowed alpha activity) one would be forced to consider seriously the possibility that alpha rhythms are strongly dependent on peripheral ocular activity. If the contrary were found, a more exclusively central mechanism of the type currently assumed would probably be involved and, as a bonus, one would have a possible "channel of communication" from curarized patients.

Figure 6:
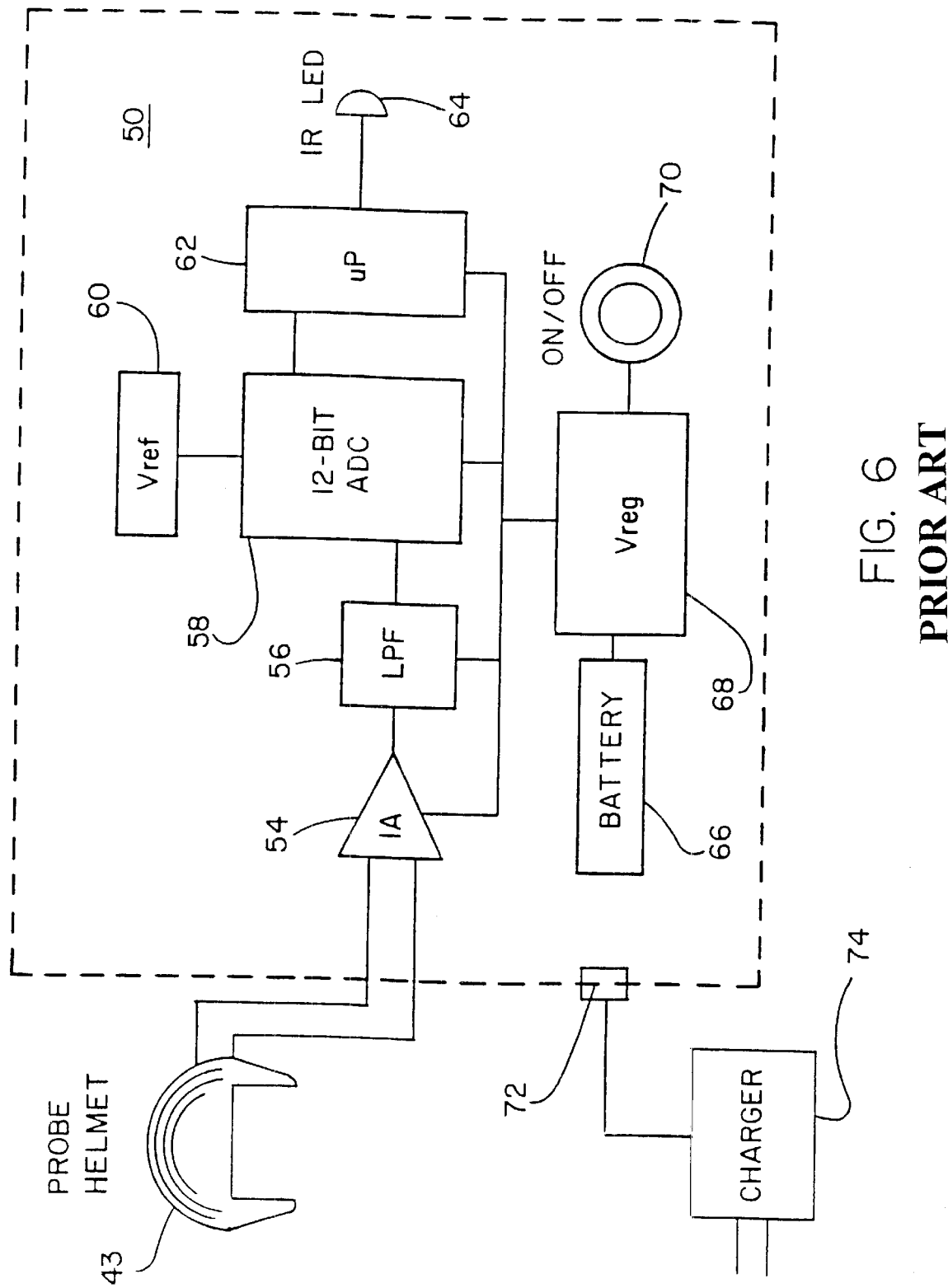
FIGS. 6 and 7 show the Freer biofeedback system that can be used by the present invention.
Figure 7:
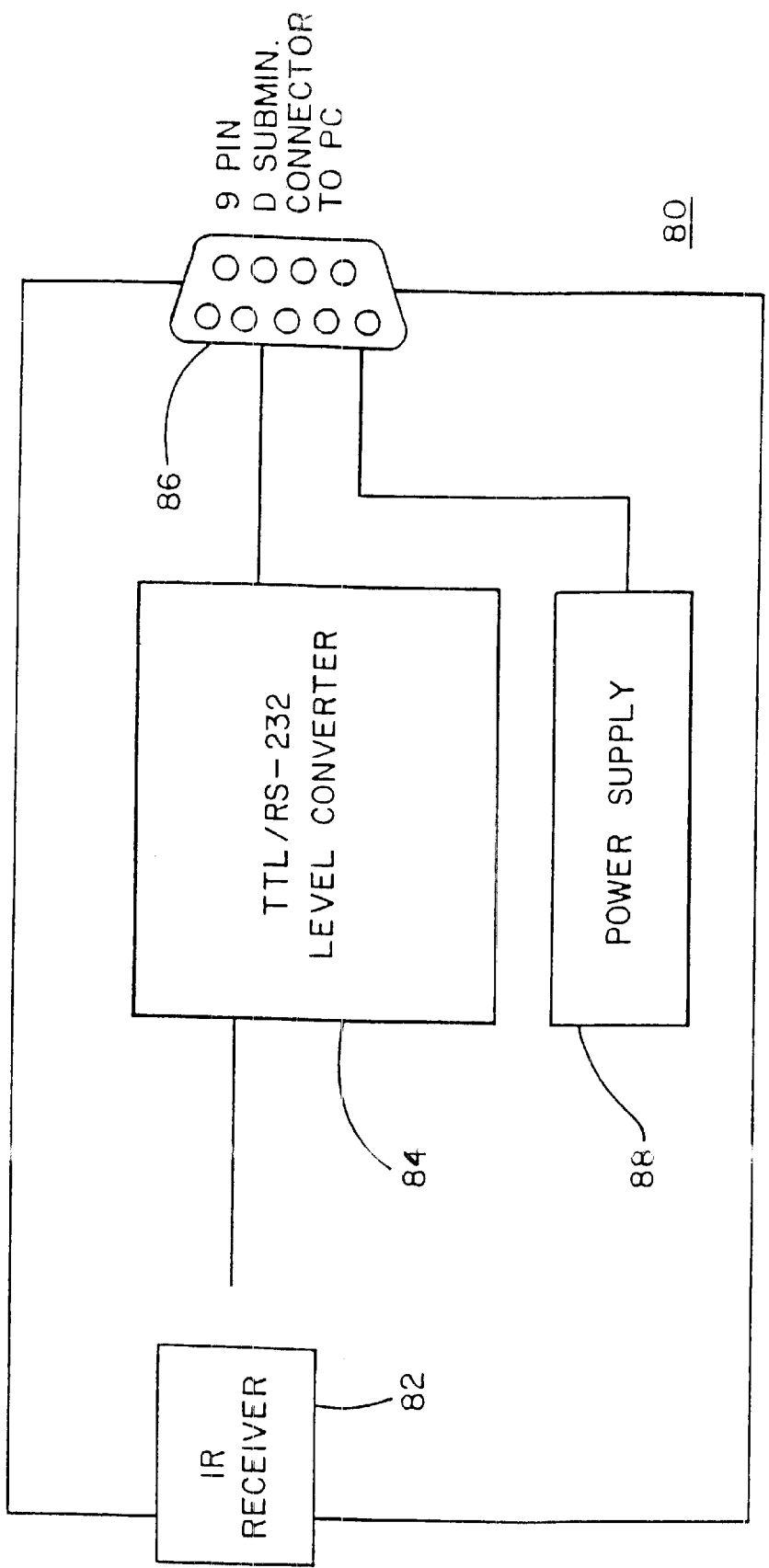

FIGS. 6 and 7 are EEG control applications from U.S. Pat. No. 6,097,981 by Peter Freer, the disclosure of which is incorporated herein by reference. The Freer system can be combined with the eye position principles to achieve a desired EEG output that makes a mental-to-optical Morse code communication system actually work.

FIG. 6 illustrates an embodiment of an infrared transmitter unit 50. The probe headpiece 43 is preferably provided with at least two electrodes. At least one of the electrodes is connected to an inverting amplifier 54 which boosts the normally weak EEG signals to improve detection and/or readability.

Figure 5:
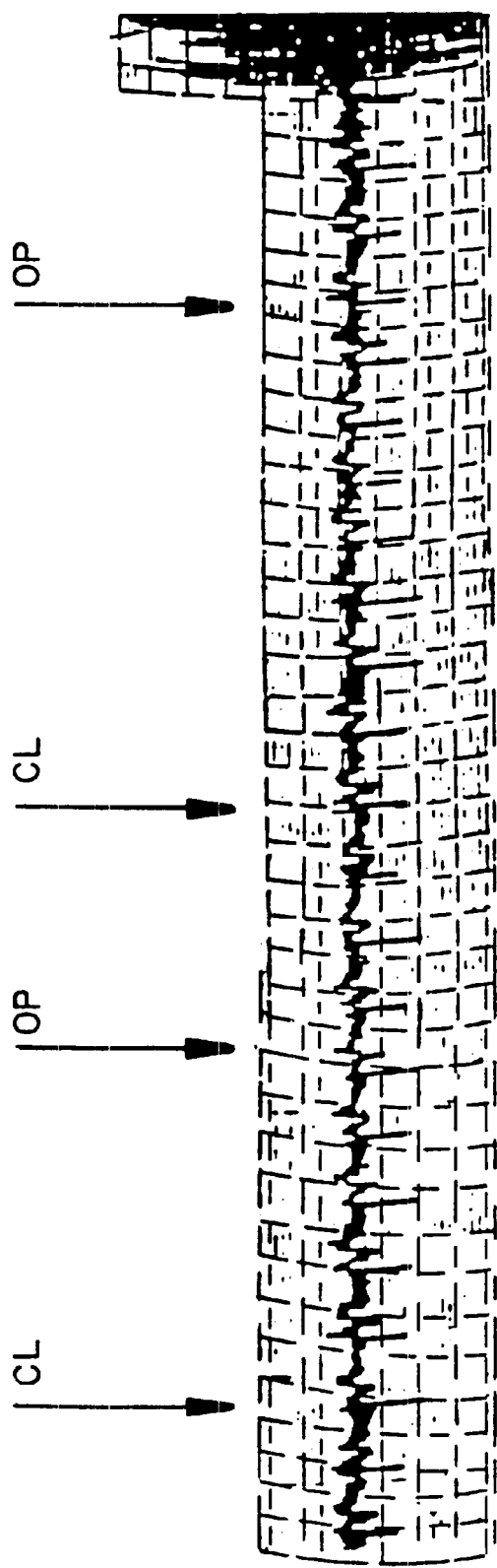
FIG. 5 is a chart of voltage signals emitted at eye opening and closure with changes in feedback signals indicative therein.

The output of the inverting amplifier 54 passes through a low pass filter 56 and is connected to a 12-bit A/D converter 58. At least one of the other electrodes supplies a reference voltage, Vref 60, which is input into the A/D converter 58. At least one other electrode serves as a ground, which is not shown in FIG. 6. Output of the A/D converter 58 is directed to a microprocessor 62 which drives an infrared LED 64 which transmits infrared signals. The unit 50 is further provided with a battery 66 whose output is passed through a voltage regulator 68 which supplied power to the inverting amplifier 54, the low pass filter 56, the A/D converter 58 and the microprocessor 62. An on/off switch 70 is provided to control the flow of electrical power from the battery 66 to the various components of the unit 50. Preferably, the battery 66 is provided with a recharging connection 72, and a battery charger 74 may be connected thereto in order to replenish the battery 66. For example, the charger 74 may convert utility line AC current to a suitable DC recharge supply. Preferably, the battery charger 74 may be disconnected from the remaining circuitry. The low pass filter 56 may be a switched capacitor. The A/D converter 58 may be a 12-bit serial multichannel converter. The microprocessor 62 may be a PIC 12C508 micro controller, which may be used to hold the parts count of the unit to a minimum. The unit 50 may operate at approximately 5 volts with a single supply, Vreg 68. The microprocessor 62 may also include control logic or control circuitry to automatically shut off power from the battery 66, for example after a certain time period has elapsed. The microprocessor 62 is preferably adapted to perform the function of separating the various bands of brain wave activity by a digital technique such as Fast Fourier Transforms (FFT). The filtering must be must be precise and selective. All of the components of FIG. 5, including the microprocessor 62, are mounted in or on the headpiece 43.

FIG. 7 schematically illustrates an infrared receiver unit 80, which may be used in conjunction with the above-described infrared transmission unit 50. The infrared receiver module 80 comprises an infrared receiver transducer 82 connected to a TDL/RS232 level converter 84. The converter 84 is connected to a 9-pin D-submin. connector 86 which is adapted for connection with a computer means such as a PC or other device. The infrared receiver unit 80 also comprises a power supply 88 which delivers power to the IR receiver 82 through the 9-pin connector 86 and the RS232 converter 84. The IR receiver transducer 82 is capable of handling at least one input signal, which corresponds to a respective EEG electrode signal that emanates from the infrared transmission unit 50. Outputs from the IR receiver transducer 80 are directed into the 9-pin connector 86 for further transmission to a PC 38 or other device. The 9-pin connector 86 provides a standard serial output to the PC 38 or other module. Preferably, the parts count may thus be kept to a minimum.

The microprocessor 62 of the infrared transmission unit 50 is preferably set at a constant data rate transmission, e.g. at 9600 baud. The receiver 80 parses the constant data flow rate for lower FFT sampling frequencies.

Figure 2:
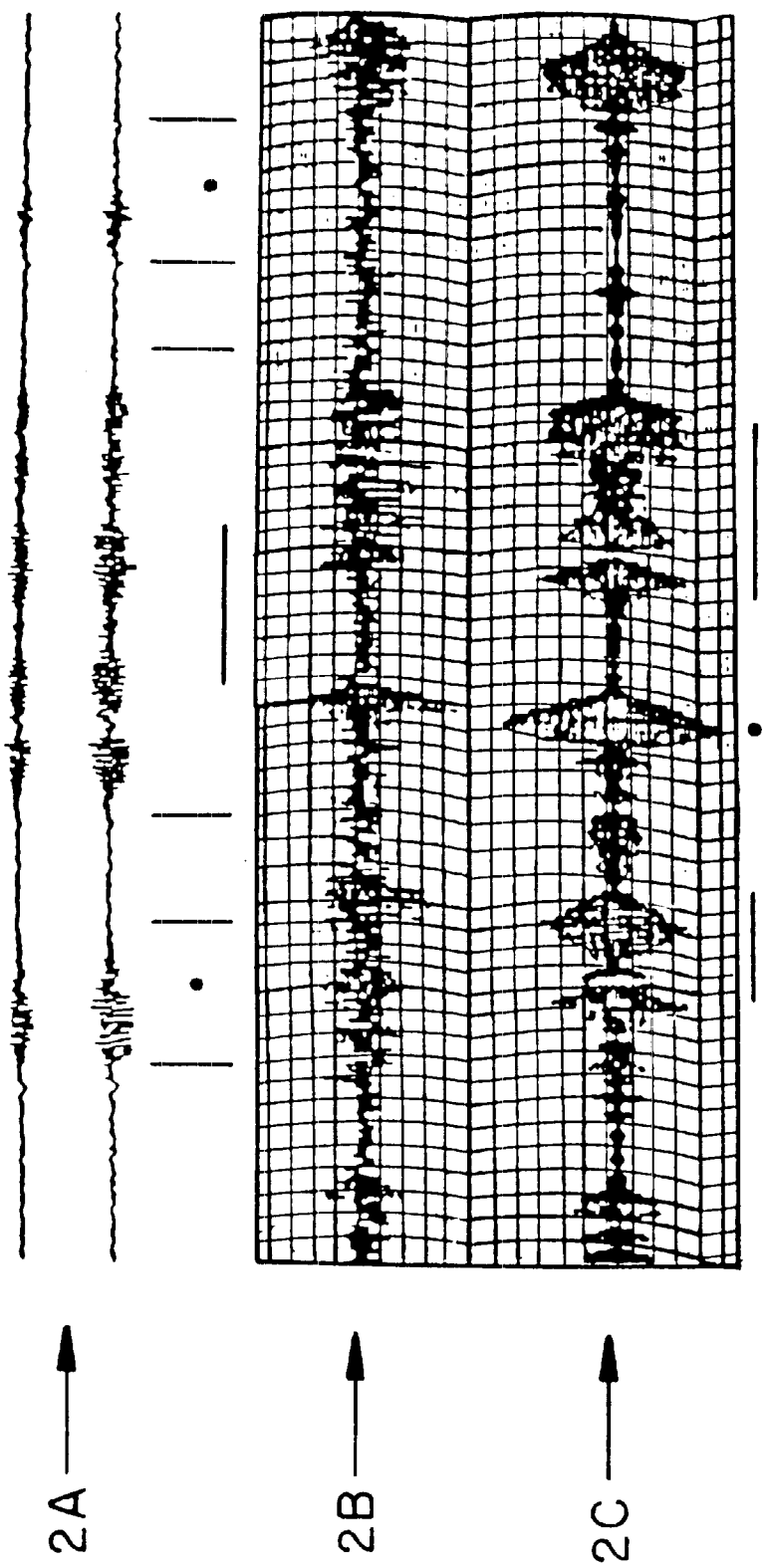
FIGS. 2a and 2b show electroencephalograph recordings of a subject actually sending Morse code.
FIG. 2c shows an effect of a filter on the signal of FIG. 2b.

Thus, as represented by FIGS. 2, 6 and 7, the present invention is particularly well suited to allow the user to actually transmit and send out a Morse code optical communication signal by means of voluntary brainwave control.

While the invention has been described in its presently preferred embodiment it is understood that the words which have been used are words of description rather than words of limitation and that changes within the purview of the appended claims may be made without departing from the scope and spirit of the invention in its broader aspects.

What is claimed is:

1. A mentally controlled optical communication system that uses volitionally altered oculomotor states to modulate an EEG control signal and activate a light transmitter, said system comprising:

a means for sensing EEG control signals from a user that has been instructed to selectively alter his alpha-wave rhythms of his brain by an eye positioning technique and produce thereby a predetermined EEG control signal pattern corresponding to a Morse code message;

a means for transmitting an optical communication signal which is activated by the EEG control signals from the sensing means; and a receiver means which receives and displays the optical communication signal of the transmitting means.

2. A brainwave controlled optical communication process that uses volitionally altered ocularmotor states to modulate an EEG control signal and activate a light transmitter, said process comprising:

instructing a user to selectively alter his alpha-wave rhythms of his brain by an eye positioning technique; and sensing EEG control signals from the user to produce a predetermined EEG control signal pattern corresponding to a Morse code message.

3. A process as defined in claim 2, wherein the sensing step comprises:

using a plurality of electrically conductive EEG electrodes placed on the user's head and which selectively block occipital alpha rhythms to produce a +1 toggle signal when blocked and a digital 0 when alpha rhythms are unblocked to thereby send Morse code signals for communication; and using an amplifier for sensing the differential voltage between at least two of said electrodes and selectively amplifying the electrical signals generated by said electrodes to produce thereby said predetermined EEG control signal.

4. A process, as defined in claim 3, wherein the user selectively blocks alpha rhythms by a controlled manipulation of oculomotor activities that include selective eye closure and eye position.

5. A process as defined in claim 4, wherein said oculomotor activities comprise eye elevation to cause alpha rhythms to appear and fixing eyes on a spot to cause alpha rhythm activities to stop.

6. A process as defined in claim 5, wherein said oculomotor activities comprise eye focusing and convergence to stop alpha rhythms and non-focusing and non-convergence to cause alpha rhythms.

* * * * *